(12) United States Patent
Donald (10) Patent No.: US 10,952,718 B2
(45) Date of Patent: Mar. 23, 2021

(54) SURGICAL RETRACTOR SYSTEM AND METHOD

(71) Applicant: Gordon D. Donald, Oceanport, NJ (US)

(72) Inventor: Gordon D. Donald, Oceanport, NJ (US)

( * ) Notice: Subject to any disclaimer, the term of this patent is extended or adjusted under 35 U.S.C. 154(b) by 135 days.

(21) Appl. No.: 16/266,582

(22) Filed: Feb. 4, 2019

(65) Prior Publication Data

US 2019/0167249 A1    Jun. 6, 2019

Related U.S. Application Data

(62) Division of application No. 14/931,461, filed on Nov. 3, 2015, now Pat. No. 10,194,896.

(60) Provisional application No. 62/074,153, filed on Nov. 3, 2014.

(51) Int. Cl.
*A61B 17/02*     (2006.01)
*A61B 17/34*     (2006.01)

(52) U.S. Cl.
CPC ...... *A61B 17/0293* (2013.01); *A61B 17/3439* (2013.01); *A61B 2017/0256* (2013.01)

(58) Field of Classification Search
CPC ...... A61B 17/02–0293; A61B 17/3439; A61B 2017/0256
USPC .................................................. 600/201–246
See application file for complete search history.

(56) References Cited

U.S. PATENT DOCUMENTS

| | | |
|---|---|---|
| 5,667,520 A | 9/1997 | Bonutti |
| 6,849,064 B2 | 2/2005 | Hamada |
| 7,318,817 B2 | 1/2008 | Hamada |
| 7,785,253 B1 | 8/2010 | Arambula et al. |
| 7,850,608 B2 | 12/2010 | Hamada |
| 7,883,522 B2 | 2/2011 | Hamada |
| 7,887,482 B2 | 2/2011 | Hamada |
| 7,935,053 B2 | 5/2011 | Karpowicz et al. |
| 7,935,054 B2 | 5/2011 | Hamada |
| 7,946,982 B2 | 5/2011 | Hamada |
| 8,298,139 B2 | 10/2012 | Hamada |
| 8,303,499 B2 | 11/2012 | Hamada |
| 8,353,826 B2 | 1/2013 | Weiman |
| 8,449,463 B2 | 5/2013 | Nunley et al. |
| 8,535,320 B2 | 9/2013 | Woolley et al. |
| 8,550,995 B2 | 10/2013 | Frasier et al. |
| 8,636,657 B2 | 1/2014 | Hamada |
| 8,827,900 B1 | 9/2014 | Pimenta |
| 9,028,522 B1 * | 5/2015 | Prado ................ A61B 17/3417 606/191 |

(Continued)

*Primary Examiner* — Nicholas J Plionis
(74) *Attorney, Agent, or Firm* — Locke Lord LLP; Scott D. Wofsy; Joshua L. Jones (57) ABSTRACT

A retractor system is provided having a plurality of blade portions that collectively present a low profile tapered configuration for insertion through tissue along a natural tissue plane. Once inserted through tissue the blade portions may be independently moved apart to form an access path to a surgical site, such as by first moving the blade portions apart along the natural tissue plane followed by moving the blade portions apart transverse to the natural tissue plane. The blade portions may be attached to retractor frame members, and rack and pinion frame components may be used to control movement of the blade portions relative to one another. Pins may be used to secure the blade portions to bone.

8 Claims, 6 Drawing Sheets

(56) References Cited

U.S. PATENT DOCUMENTS

| | | | |
|---|---|---|---|
| 2010/0217088 A1* | 8/2010 | Heiges | A61B 17/0218 600/207 |
| 2012/0088979 A1* | 4/2012 | Nunley | A61B 17/0206 600/231 |
| 2012/0310048 A1* | 12/2012 | Siegal | A61B 17/025 600/206 |
| 2013/0018408 A1* | 1/2013 | Farley | A61B 17/0206 606/198 |
| 2014/0180016 A1 | 6/2014 | Miles et al. | |
| 2014/0288375 A1 | 9/2014 | Miles et al. | |
| 2014/0316209 A1* | 10/2014 | Overes | A61B 17/0293 600/206 |
| 2015/0045626 A1 | 2/2015 | Reimels | |

\* cited by examiner

SURGICAL RETRACTOR SYSTEM AND METHOD

CROSS-REFERENCE TO RELATED APPLICATIONS

This application is a divisional of U.S. patent application Ser. No. 14/931,461 filed Nov. 3, 2015, which claims benefit of priority to U.S. Provisional Patent Application Ser. No. 62/074,153 filed Nov. 3, 2014, each of which is incorporated by reference herein in its entirety.

BACKGROUND

Technical Field

The present disclosure relates to surgical retraction, and more particularly, to a minimally invasive retractor for spine surgery, including lateral access surgery.

Background of Related Art

In connection with surgery on the human spine, accessing the spine may be difficult and complex, and traditional open access through many layers of soft tissue contributes to post surgery pain and discomfort, and may prolong recovery and impede favorable results of surgery.

Attempts have been made to make retractors which provide less disruptive access through soft tissue to reach the spine. Examples include Hamada U.S. Pat. Nos. 6,849,064; 7,318,817; 7,883,522; 7,935,054; 7,887,482 all entitled "Minimal Access Lumbar Diskectomy Instrumentation and Method", and Hamada U.S. Pat. Nos. 7,850,608; 7,946,982; 8,636,657; 8,298,139; and 8,303,499 all entitled "Minimal Incision Maximal Access MIS Spine Instrumentation and Method", all of which are incorporated herein by reference.

In so-called lateral access or trans-psoas muscle spine surgery the spine is approached from a lateral direction, from the side of the patient. In this approach, access typically must be gained through the psoas muscle in order to reach the spine. Retractors used for such lateral access surgery include the Maximum Access Surgery (MAS®) platform from Nuvasive, Inc. (San Diego, Calif.), the MARS™3V system from Globus Medical, Inc. (Audubon, Pa.), the Pipeline LS from Depuy Synthes Spine (Raynam, Mass.) and the Direct Lateral Interbody Fusion (DLIF) system from Medtronic Sofamor Danek (Memphis, Tenn.). The following patents and published patent applications may show or describe these commercially available systems. Arambula U.S. Pat. No. 7,785,253 entitled "Surgical Access System and Related Methods"; Wooley U.S. Pat. No. 8,535,320 entitled "Method and Apparatus for Performing Spinal Surgery"; Miles U.S. Published Patent Applications 2014/0180016 and 2014/0288375, both entitled "Surgical Access System and Related Methods"; Pimenta U.S. Pat. No. 8,827,900 entitled "Surgical Access System and Related Methods"; Frasier U.S. Pat. No. 8,550,995 entitled "Surgical Access Devices and Methods of Minimally Invasive Surgery"; Karpowicz U.S. Pat. No. 7,935,053 entitled "Surgical Retractor System"; and Weiman U.S. Pat. No. 8,353,826 entitled "Tissue Retractor and Method of Use". The foregoing patents and applications are incorporated herein by reference.

The foregoing lateral access systems typically use a plurality of sequentially dilating cannulas of increasing outer diameter inserted one over another to create an initial access path to the spine. Once the last dilating cannula is in place, a retractor assembly is inserted over the dilating cannula, and is operated to move the retractor blades apart in a generally radial direction to spread soft tissue and create a working path to the spine. Sequentially dilating cannulas, followed by radial retraction is not an efficient means to create a working path to the spine, and spreading the soft tissue and the psoas muscle in this manner is more traumatic to the tissue than necessary, and may prolong recovery.

The Ravine® retractor system available from K2M, Inc. (Leesburg, Va.) is a substantial improvement in lateral spinal access retraction. The Ravine retractor system and method of use are described in Nunley U.S. Pat. No. 8,449,463 entitled "Lateral Access System and Methods of Use", which is incorporated herein by reference. In the Ravine system, the retractor has two slim profile blades that are inserted through soft tissue over a previously placed pin or wire with the retractor blades aligned with the fibers of the psoas muscle. The retractor blades pass between the fibers of the muscle with reduced trauma to the muscle, and without any need for sequentially dilating cannulas. Once the Ravine retractor is inserted, it is rotated ninety degrees to orient the blades transverse to the psoas muscle. The retractor blades are then spread apart to retract tissue and create a working path to the spine. While the Ravine system is a significant improvement over other lateral access retractors, a degree of trauma, albeit less than with other retractors, is introduced by rotating the retractor blades ninety degrees to split the psoas muscle, and then spreading the retractor blades apart.

Thus, a need exists for an improved retractor system to access the spine with minimal trauma to soft tissue.

SUMMARY OF THE INVENTION

A retractor includes at least four retractor blades assuming a closed configuration having a low profile to facilitate insertion through tissue along a natural tissue plane. The blades have an expanded configuration to retract tissue and provide access to a surgical site.

The retractor can include a frame or tool for controlling individual movement of the blades toward and away from one another. The blades in the closed configuration can define a substantially oblong cross-sectional profile to facilitate insertion through muscle fibers. The blades can define retractor quadrants that assume a closed configuration in which the cross-sectional configuration of the retractor has a first maximum dimension along one axis and a second maximum dimension along a second axis transverse to the first axis, the first dimension being greater than the second dimension.

Each quadrant blade can define a cross section having a substantially straight section along an internal edge in a first direction, a substantially straight edge along a second internal surface in a second direction substantially perpendicular to the first direction, and an arcuate or oblique/tapered external edge connecting the external termination points of the internal edge and the straight edge. For each cross section, an inner arcuate edge can connect the internal edge to the straight edge. The arcuate edges of the blades can define a longitudinal through bore when the blade portions are in the closed configuration. The through bore can be configured and dimensioned to accommodate a guide wire or guide pin.

A cam mechanism can be included in a distal tip of the retractor blades in the closed configuration, wherein the cam mechanism is configured so rotation of a cam of the cam mechanism forces the blades apart. A cam of the cam mechanism can be positioned so rotation of the cam about a wire extending longitudinally through the blades forces the blades apart.

A method of performing surgery can include providing a surgical retractor having at least four retractor blades assuming a closed configuration having a low profile to facilitate insertion through tissue along a natural tissue plane, and an expanded configuration to retract tissue and provide access to a surgical site, the retractor in the closed configuration having a length in a first direction that is greater than the width of the retractor transverse to the length. The method includes inserting the retractor into tissue in the closed position with the length in the first direction aligned with muscle fibers of the tissue so as to insert the retractor in the closed configuration between tissue fibers until the tip of the retractor reaches a surgical site. The method also includes moving the blades apart to divide the tissue fibers along the natural tissue plane of the tissue fibers and to retract tissue to form an access path to the surgical site.

Moving the blades apart can include moving the blades apart along the natural plane of muscle fibers to divide muscle tissue along the natural tissue plane of a muscle, followed by the moving the blade portions apart substantially perpendicular to the natural tissue plane of the muscle fibers. Moving the blades apart can include initially separating the blades using a cam mechanism in the proximate tip of the blades. Separating the blades using a cam mechanism can include rotating a cam of the cam mechanism about a wire extending longitudinally through the blades. Moving the blades apart can include after initially separating the blades, using a tool to further separate the blades in along the natural plane of muscle fibers.

Moving the blades apart can include using a tool to apply a distracting force outward against the blades at the distal tip of the retractor blades. Moving the blades apart can include moving each blade independent of the other blades. Moving blades apart to divide tissue fibers can include first moving two pairs of the blades apart from one another along the first direction and then separating the blades in each pair from one another in a direction transverse to the first direction to form the access path. The method can include inserting a pin though a hole in a respective one of the blades to anchor the respective blade to bone. It is also contemplated that the method can include mounting the blades to a frame at proximal ends of the blades.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION

Figures 1A, 1B:
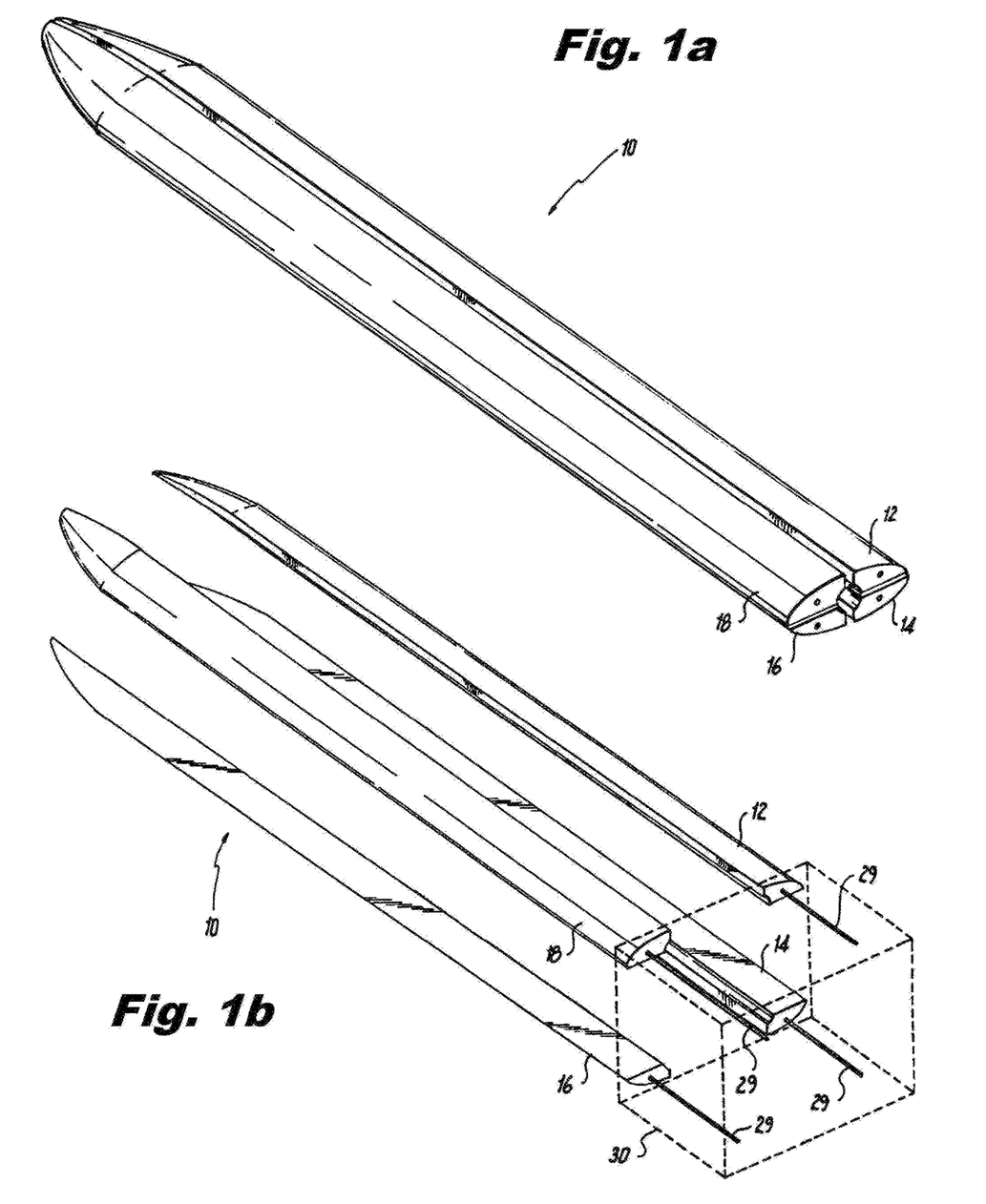
FIG. 1*a* is a perspective view of an exemplary embodiment of a retractor blade assembly constructed in accordance with the present disclosure, showing the retractor blades in a closed configuration.
FIG. 1*b* is a perspective view of the assembly of FIG. 1, showing the blades in a retracted configuration for surgical access.

Reference will now be made to the drawings wherein like reference numerals identify similar structural features or aspects of the subject disclosure. For purposes of explanation and illustration, and not limitation, a partial view of an exemplary embodiment of a retractor blade assembly in accordance with the disclosure is shown in FIG. 1A and is designated generally by reference character 10. Other embodiments of retractor blade assemblies in accordance with the disclosure, or aspects thereof, are provided in FIGS. 1B-4D, as will be described. The systems and methods described herein can be used to retract tissues, e.g., soft tissues, for surgical access. The systems and methods disclosed herein may find application in any retraction situation where it is desirable to insert the retractor aligned the muscle fibers. One such application is a lateral, trans psoas approach to the spine. For convenience the systems and methods disclosed herein are described in the exemplary context of trans psoas applications, but this disclosure is not limited to this exemplary context.

Retractor blade assembly 10 includes four quadrant blades 12, 14, 16, 18. Optionally, each quadrant blade may have a longitudinal through hole 20, 22, 24, 26, respectively, and/or a groove on an inner edge thereof configured and dimensioned to receive a guide wire or pin therethrough.

Figure 2:
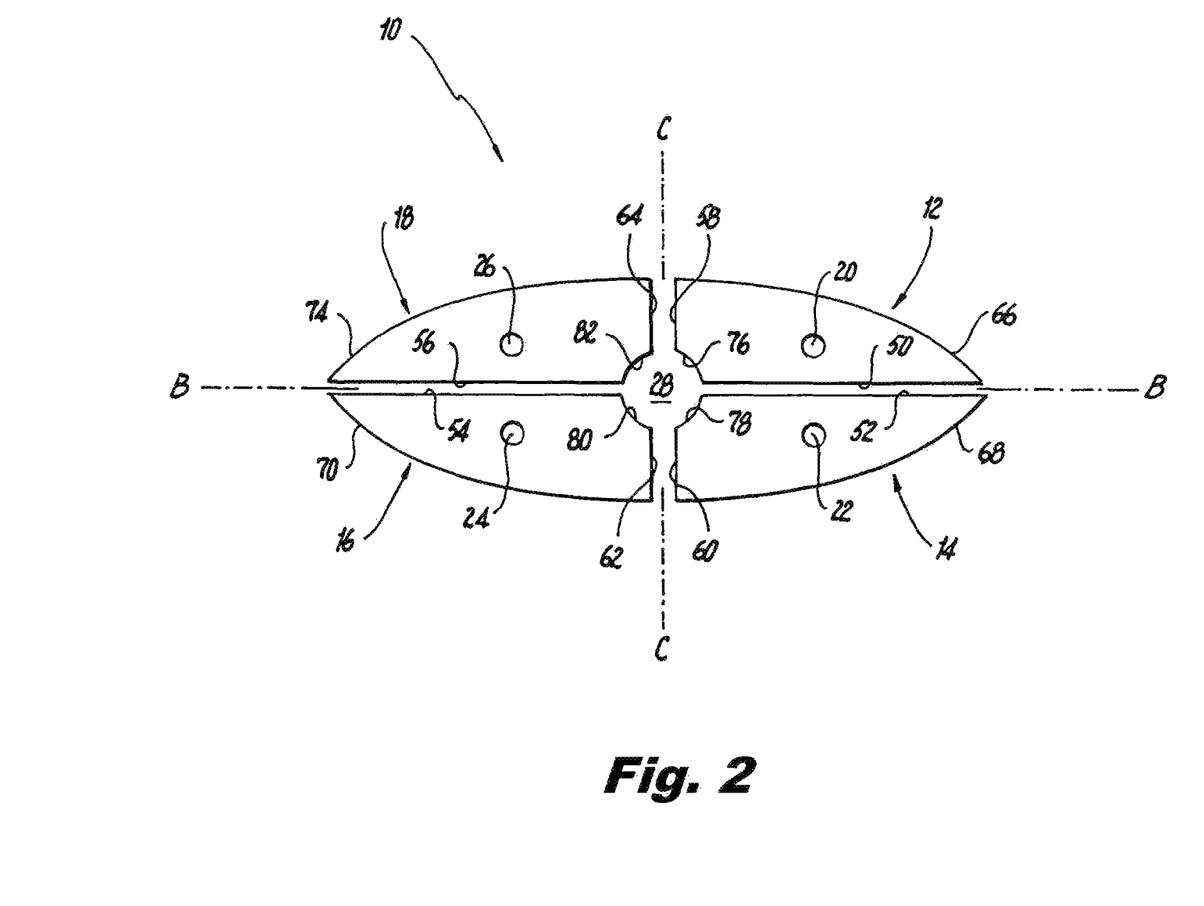
FIG. 2 is a cross-sectional end view of the blade assembly of FIG. 1, showing the cross sections of the individual blades.

Each quadrant blade 12, 14, 16, 18 defines a cross section, shown in FIG. 2, having a substantially straight section along a respective internal edge 50, 52, 54, 56 in the first direction, e.g., the direction along axis B-B. Each cross section also has a substantially straight edge 58, 60, 62, 64 along a respective second internal surface in a second direction substantially perpendicular to the first direction, e.g., the direction along axis C-C. Each cross section also has an arcuate or oblique/tapered external edge 66, 68, 70, 74 along a respective external surface connecting the external termination points of the first and second surfaces corresponding to the respective internal edges 50, 52, 54, 56, and the respective straight edges 58, 60, 62, 64. A respective inner arcuate section or edge 76, 78, 80, 82 connects each of the respective internal edges 50, 52, 54, 56 to a respective one of the straight edges 58, 60, 62, 64.

Alternatively or in addition, the center of the blade assembly 10 where the quadrant blades 12, 14, 16, 18 meet may be configured to define a through passage 28 defined by inner arcuate edges 74, 76, 78, 80 for passage of a guidewire or pin when the quadrant blades 12, 14, 16, 18 are in the closed or approximated position shown in FIGS. 1*a* and 2. Each quadrant blade 12, 14, 16, 18 is separate from the other quadrant blades and is independently controlled to selectively spread apart in multiple directions. The movement of the quadrant blades 12, 14, 16, 18 is controlled by a frame structure 30 outside the body, such as a frame having one or more rack and pinion arrangements to controllably move the quadrant blades apart from one another and maintain their relative position. It is contemplated that one or more rack and pinion frame structures, such as those described in Jako U.S. Pat. Nos. 5,503,617 and 5,813,978 both entitled "Retractor and Method for Direct Access Endoscopic Surgery", both of which are incorporated herein by reference, the Hamada and Nunley patents referred to above may be adapted to permit individual selective movement of each quadrant blade independent of the other quadrant blades.

With continued reference to FIG. 2, which is a cross-section view taken along line A-A of FIG. 1, the cross-sectional configuration of the blade shows that the quadrant blades 12, 14, 16, 18 collectively define a low profile configuration that is insertable through the psoas muscle with the axis B-B aligned with the muscle fibers. In the closed configuration shown in FIGS. 1a and 2, the length of the retractor along axis B-B is greater than the width of the retractor along axis C-C. The length of the retractor along axis B-B and the thickness of the blades along axis C-C are selected so that the blades in the closed position may be inserted between fibers of the psoas muscle without significant dilation and without inserting the retractor over previously inserted dilators. One or more dilators may be used to pre-dilate the space to receive the retractor, as contemplated in Nunley U.S. Pat. No. 8,449,463, but such dilators are preferably used only to loosen the tissue to receive and accept the retractor, but are removed prior to insertion of the retractor, such that the retractor is inserted directly into the muscle and not over such dilators. As previously discussed, the retractor may be inserted over a pin or guidewire. In the closed position shown in FIGS. 1a and 2, retractor 10 has a maximum overall length along axis B-B of about 40 mm and a maximum width along axis C-C of about 10 mm, however, any other suitable size can be used for a given application. In addition, the distal tip of the retractor is tapered, as shown, so that the tip and tapered sides of the retractor facilitate insertion of the retractor through muscle tissue in the closed position. The overall length of the retractor quadrant blades 12, 14, 16, 18 is any suitable size sufficient to reach the surgical site and extend out of the soft tissue, and may range from about 1 cm to about 25 cm, for example.

Figures 3A, 3B:
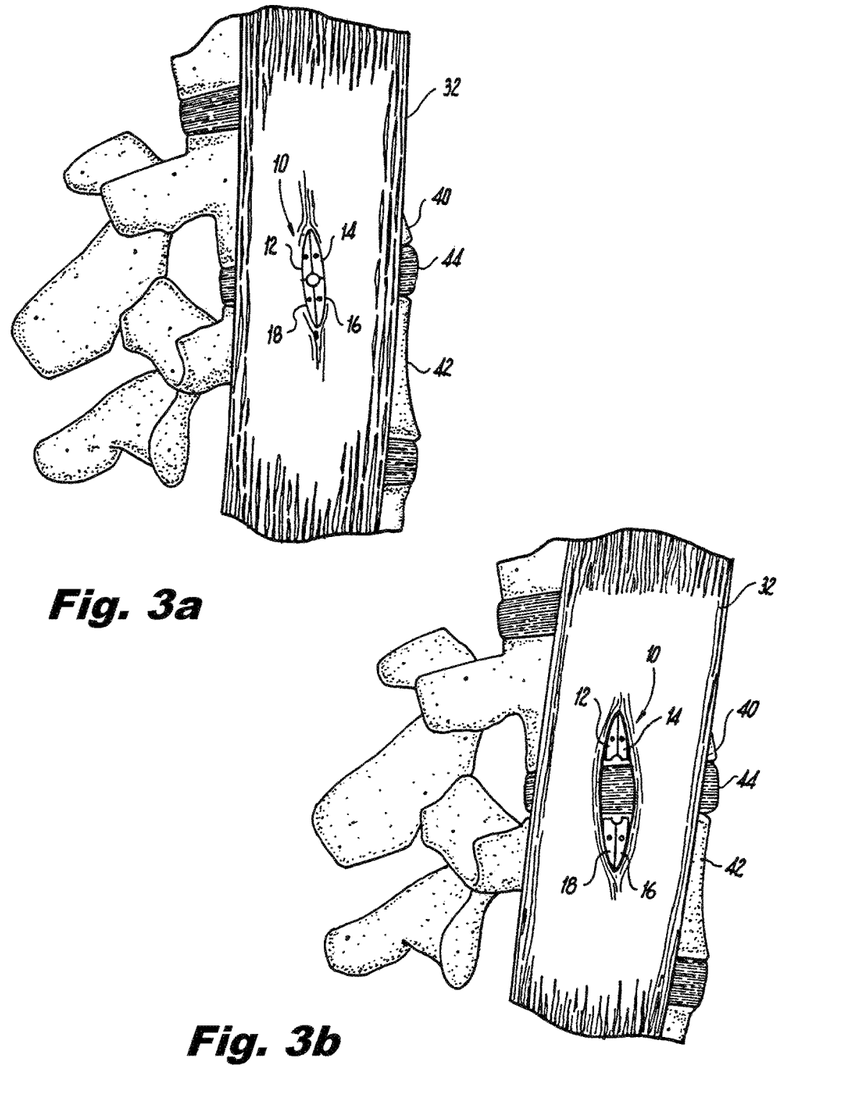
FIGS. 3A-3D are transverse views of the assembly of FIG. 1, sowing stages in the use of the blade assembly to retract tissue for surgical access to a spinal disc.
Figures 3C, 3D:
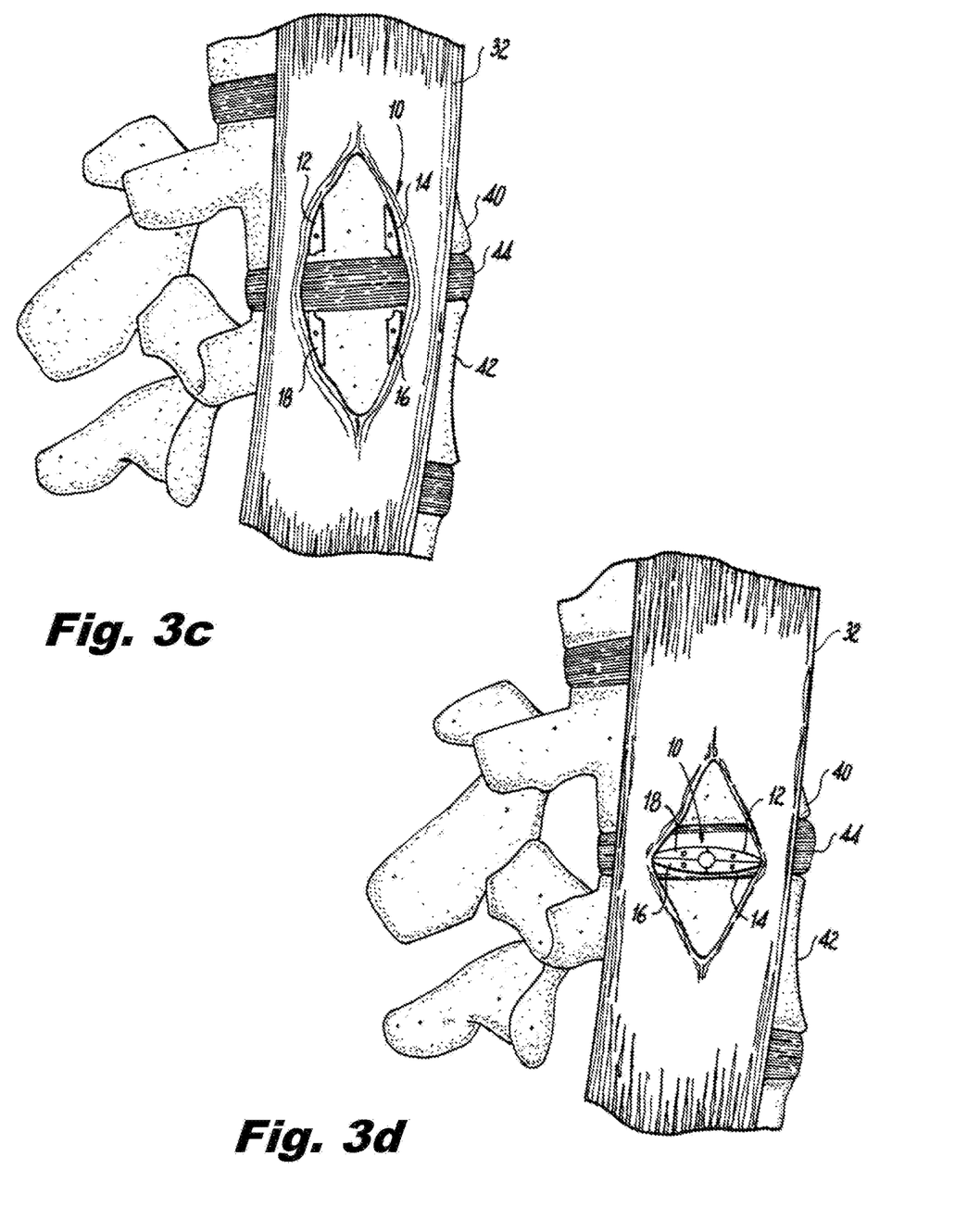

Referring now to FIGS. 3A-3C, the insertion and function of the retractor assembly will now be described. In FIGS. 3A-3C, the retractor blades are shown relative to two adjacent vertebrae 40, 42, a spinal disc 44 between the vertebrae and soft tissue and muscle to be divided and retracted in order to provide access to the spine, particularly the spinal disc, for spine surgery. For convenience and by way of example, the use of the retractor is described in connection with a lateral surgical approach to the spine through the psoas muscle. However, it is contemplated that the retractor blade assembly may have application in other surgical settings.

As shown in FIG. 3A, the retractor blades are inserted through the psoas muscle 32 with the blades in a closed, approximated configuration. The muscle may be digitally or manually probed or otherwise dissected to facilitate insertion of the retractor blades. Such dissection may involve inserting one or more probes and/or distractors to loosen tissue and facilitate insertion of the retractor blades through the muscle. Optionally, a guide wire or pin may be placed into the disc or bone to guide the path of the retractor. In such case, the guidewire or pin would be received through the openings 20, 22, 24, 26 or through the center 28 of the closed blades.

Once the retractor blades have been inserted to the desired depth, the blade portions may be spread apart in a controlled fashion to retract tissue and provide a working opening to the surgical site, with reduced trauma to tissue. By way of example, in a preferred method shown in FIGS. 3A-3C, quadrant blades 12, 14 may be moved apart from quadrant blades 16, 18 along axis B-B, which is aligned with the direction of the muscle fibers to first divide the quadrant blades along the natural plane of the muscle tissue. In this manner the muscle advantageously is divided along the plane of muscle fibers. When the quadrant blades overlie desired portions of the vertebral bodies (see FIG. 3B), the blade pairs 12, 18 and 14, 16 may be separated along axis C-C, which defines a path substantially perpendicular to axis B-B, in order to retract tissue that has previously been divided along the plane of the muscle fibers to create and maintain an access path to the surgical site, illustrated as a spinal disc, as shown in FIG. 3C.

One or more quadrant blades may be secured to bone by inserting a pin 29, shown in FIG. 1b, through the central opening 20, 22, 24, 26 of the respective quadrant blade 12, 14, 16, 18. Thus, for example, one or some or all of quadrant blades shown in FIG. 3C may be secured to bone and maintained in position to maintain the positional relationship of the quadrant blades relative to each other and to the bone and, hence, the surgical site. It is contemplated that the pins 29 used to anchor the blade or blades in place may have a threaded or possibly self-tapping threaded tip. It is also contemplated that one or more pins 29 may be placed before the quadrant blades are spread apart, or after the quadrants are partially spread apart, so as to provide controlled retraction and possibly to leverage retraction in a specific direction relative to the pinned quadrant blade(s). In this regard, it may be desirable to maintain the position of one quadrant relative to bone while spreading apart the other quadrant retractor blades, in order to optimize the position of the quadrant retractor blades and, hence, the retracted soft tissue, relative to the surgical site. It is also contemplated that the shape of the tip portion of each retractor quadrant blade may be selected to conform to the shape of the underlying bony structure, so that the retractor blade conforms to the bone surface and minimizes the possibility that tissue may work its way under the retractor blades into the operative area.

As will be appreciated, many variations of the blades and their use are possible. In the broadest sense, the retractor consists of a number (preferably four) of blade portions which assume a closed position configuration in which the blade portions in the aggregate present a thin, low profile tapered blade retractor that is readily inserted through tissue along the natural plane of muscle tissue. Preferably, any dilation prior to insertion of the retractor is digital or with low profile probes and/or dilators, similar to those disclosed in Nunley U.S. Pat. No. 8,449,463. Advantageously, the blades may be inserted without dilating structure in place in the tissue. That is, the retractor need not be inserted over a distraction member or members, as is commonly the practice with many existing lateral access retraction systems, where the retractor is inserted over previously inserted dilator(s).

It will also be understood that the quadrant blades may be spread apart in any desired orientation, order or sequence. Thus, blade pairs 12, 14 and 16, 18 need not be spread apart longitudinally along axis B-B before being spread apart transversely along axis C-C. Indeed, the quadrant blades may spread apart fully or partially in the transverse direction and then in the longitudinal, or any combination of partially expanding the blades to gradually or sequentially reach full expansion. Moreover, the blade portions need not be moved in parallel. Rather, each blade portion may be controlled and moved apart separate from the movement of each of the other blade portions so that the surgeon can optimally retract tissue and orient and maintain the position of the retractor in tissue relative to bone and the disc space.

Unlike the Ravine retractor, which must be rotated ninety degrees before separating the blades, the present retractor does not need to be rotate ninety degrees prior to separating the blades. The separation of the blade portions of the present retractor without rotating the retractor ninety degrees provides greater control to the surgeon during retraction and reduces trauma to the tissue to be retracted. However, as shown in FIG. 3D, optionally the retractor quadrant blades can be rotated ninety degrees relative to the muscle fibers to initiate separation along the muscle fibers, after which the blades can be rotated back to the initial position for separation of the blades as shown in FIG. 3B.

In another exemplary embodiment, a method for use of a four bladed retractor includes placing a single tube guidewire cannula, confirming the guidewire position fluoroscopically, and placing the guidewire is in the disk space, or other surgical site or target. Retractor blades, e.g., quadrant blades 12, 14, 16, 18, are placed over the guidewire as a unitary device consisting of two pairs of retractor blades. Each pair is initially translated generally cephalad and caudad, e.g., as indicated in FIG. 3B. Each pair of blades is then split to translate generally medial and lateral, e.g., as indicated in FIG. 3C. Although this scenario describes a rectangular surgical portal as an example, those skilled in the art will readily appreciate that the blades may be of any suitable geometric configuration thereby resulting in any suitable non-rectilinear retraction portal.

Figures 4A, 4B:
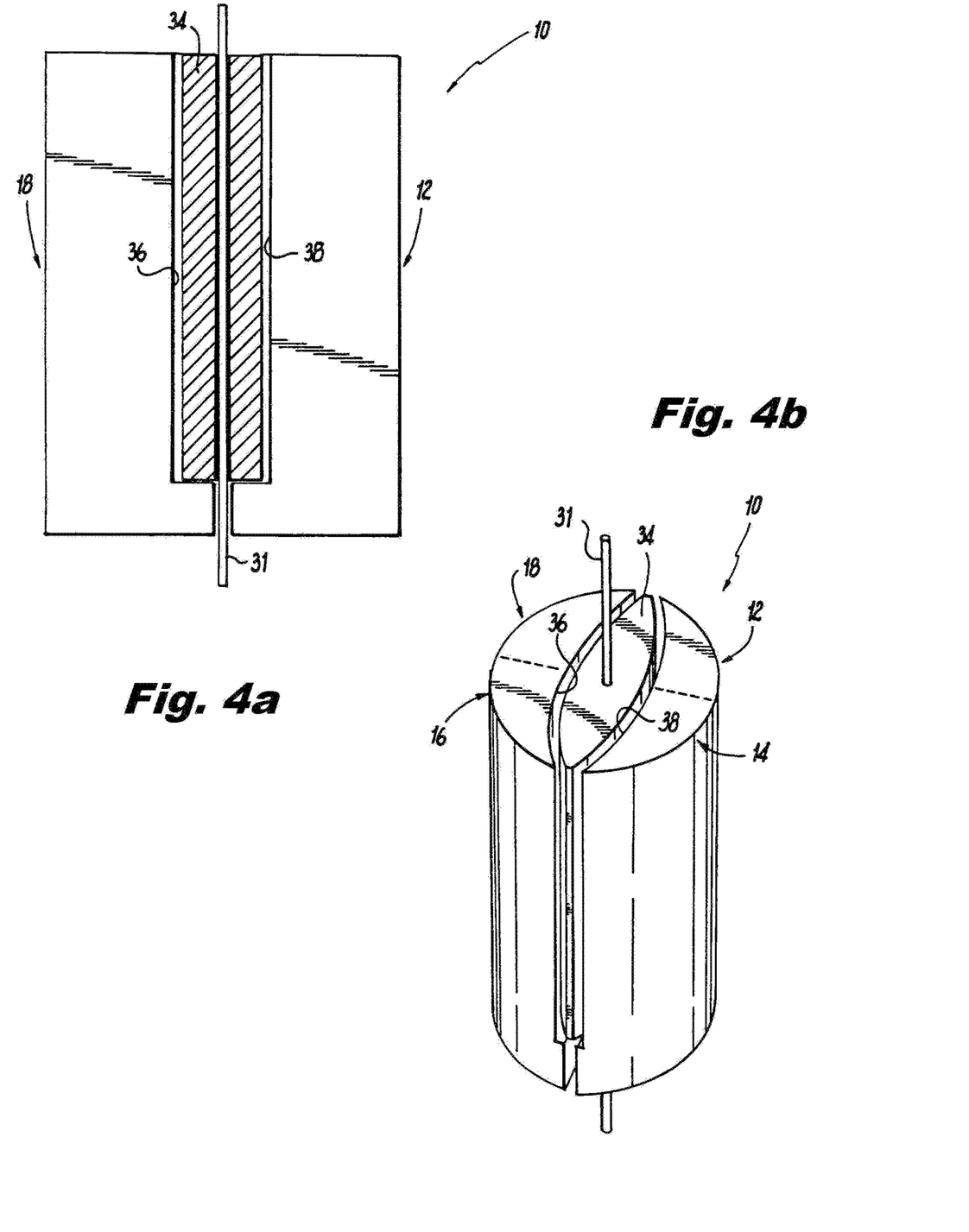
FIGS. 4A-4B are schematic views, cross-sectional and perspective, respectively, showing a cam mechanism in the distal tip of the blade assembly of FIG. 1 with the blades in the closed configuration.
Figures 4C, 4D:
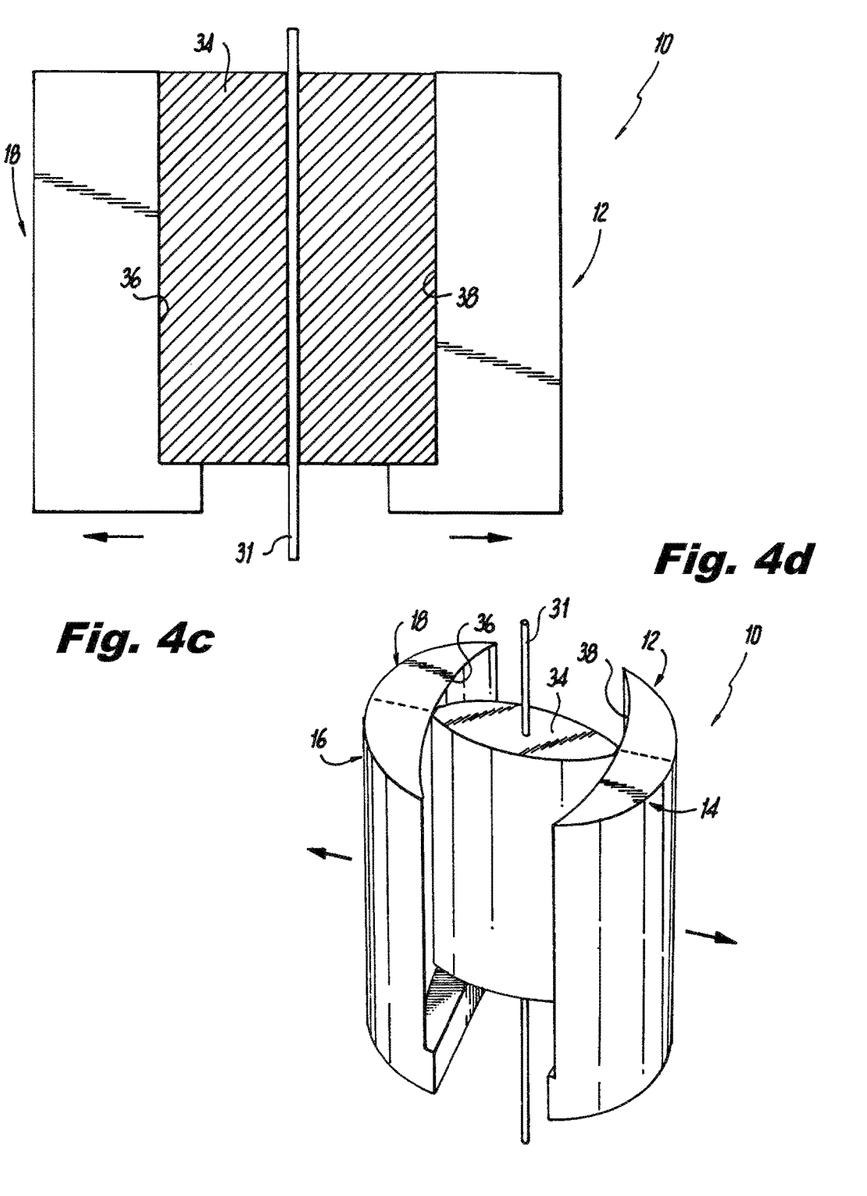
FIGS. 4C-4D are schematic views, cross-sectional and perspective, respectively, showing the cam mechanism in the distal tip of the blade assembly of FIG. 1 with the blades after initial separation.

With reference now to FIGS. 4A-4D, the initial separating of cephalad and caudad blade pairs is important to provide working room for a distractor type tool that provides a distractor force at the distal end (anatomic target) of the blades. This initial separation can be provided by a rotating cam 34 that is designed to be part of the initial unitary confluence of all four retractor quadrant blades 12, 14, 16, 18, e.g, in a cavity formed between surfaces 36 and 38 in the distal end of passage 28 (identified in FIG. 2). FIGS. 4A and 4B show cam 34 and the distractor blades in their initial, unexpanded state. By rotation of cam 34 about wire 31 extending longitudinally through the blades, the initial distraction of quadrant blades 16 and 18 from quadrant blades 12 and 14 can be accomplished, as shown in FIGS. 4C and 4D. A frangible connection can initially connect the blades together, which can be broken during the initial separation. Those skilled in the art will readily appreciate that cam 34 is exemplary, and that any other suitable tool can be used for the initial separation depicted in FIGS. 4A-4D.

After the initial separation illustrated in FIGS. 4A-4D, any other suitable tool can be used that can provide mechanical separation of quadrant blades 12, 14, 16, 18 in a number of different planes. For instance a tool may be designed with a single or double action scissoring mechanism to separate either the blade pairs or individual blades. Another embodiment may be a mushroom base instrument activated with a screw type mechanism or an instrument such as a cannula over the guidewire with deployable mechanisms converting longitudinal translation down the cannula to horizontal translation distracting the retractor blades.

Applying the distraction forces outward against quadrant blades 12, 14, 16, 18 at the distal tip thereof, as opposed to at an external frame at the proximal end thereof, reduces the amount of material strength required for the quadrant blades 12, 14, 16, 18 relative to what would be required if the forces were applied at the proximal end. This makes it possible to fabricate quadrant blades 12, 14, 16, 18 from disposable materials such as polymers, and provides the potential advantages of disposability.

The blade pairs and individual blades are manipulated by one or multiple devices/tools that control the blade at its distal end (near the anatomic target) and so as to provide anatomic retraction and visualization for the surgical procedure being performed. Once suitably positioned each individual quadrant blade 12, 14, 16, 18 can be fixated to the target tissue, e.g., bone or soft tissue. Each quadrant blade 12, 14, 16, 18 can then now be fixated or locked into a proximal stationary frame, e.g., frame 30 shown in FIG. 1b, or ring external to or immediately at the wound or opening of surgical portal. In the example depicted in FIG. 1a, quadrant blades 12, 14, 16, 18 are attached to a multiply adjusted rectangular frame 30 allowing for complete freedom of movement (translation and rotation) of each individual quadrant blade 12, 14, 16, 18. Additionally, although the quadrant blades 12, 14, 16, 18 are shown and described as having a fixed length, blades may be allowed to have variable length by either a telescoping mechanism or a multi-segmental mechanism, or any other suitable mechanism, thus decreasing need for extensive inventory with multiple sizes.

The methods and systems of the present disclosure, as described above and shown in the drawings, provide for surgical retraction with superior properties including reduced trauma and disposability. While the apparatus and methods of the subject disclosure have been shown and described with reference to preferred embodiments, those skilled in the art will readily appreciate that changes and/or modifications may be made thereto without departing from the scope of the subject disclosure.

What is claimed is:
1. A method of performing surgery comprising:
providing a surgical retractor having at least four retractor blades assuming a closed configuration having a low profile to facilitate insertion through tissue along a natural tissue plane, and an expanded configuration to retract tissue and provide access to a surgical site, the retractor in the closed configuration having a length in a first direction that is greater than the width of the retractor transverse to the length;
inserting the retractor into tissue in the closed position with the length in the first direction aligned with muscle fibers of the tissue so as to insert the retractor in the closed configuration between tissue fibers until the tip of the retractor reaches a surgical site; and
moving the blades apart to divide the tissue fibers along the natural tissue plane of the tissue fibers and to retract tissue to form an access path to the surgical site,
wherein moving the blades apart includes initially separating the blades using a cam mechanism in a proximate tip of the blades, wherein separating the blades using a cam mechanism includes rotating a cam of the cam mechanism about a wire extending longitudinally through the blades.
2. The method as recited in claim 1, wherein moving the blades apart includes moving the blades apart along the natural plane of muscle fibers to divide muscle tissue along the natural tissue plane of a muscle, followed by the moving the blade portions apart substantially perpendicular to the natural tissue plane of the muscle fibers.

3. The method as recited in claim 1, wherein moving the blades apart includes after initially separating the blades, using a tool to further separate the blades in along the natural plane of muscle fibers.

4. The method as recited in claim 1, wherein moving the blades apart includes using a tool to apply a distracting force outward against the blades at a distal tip of the retractor blades.

5. The method as recited in claim 1, wherein moving the blades apart includes moving each blade independent of the other blades.

6. The method as recited in claim 1, wherein moving blades apart to divide tissue fibers includes first moving two pairs of the blades apart from one another along the first direction and then separating the blades in each pair from one another in a direction transverse to the first direction to form the access path.

7. The method of claim 1, further comprising:
   inserting a pin though a hole in a respective one of the blades to anchor the respective blade to bone.

8. The method of claim 1, further comprising mounting the blades to a frame at proximal ends of the blades.

\* \* \* \* \*